United States Patent [19]

Maeda et al.

[11] 4,259,105

[45] Mar. 31, 1981

[54] DIPHENYLAMINE DERIVATIVES

[75] Inventors: Kuniyasu Maeda, Yokohama; Minoru Kaeriyama, Odawara; Nobuo Matsui, Odawara; Hisao Ishikawa, Odawara; Shozo Yamada, Hiratsuka; Susumu Okunuki, Ohisomachi, all of Japan

[73] Assignee: Nippon Soda Company, Ltd., Ohtemachi, Japan

[21] Appl. No.: 33,682

[22] Filed: Apr. 26, 1979

[30] Foreign Application Priority Data

May 10, 1978 [JP] Japan .................. 53-54458
Sep. 13, 1978 [JP] Japan .................. 53-112630
Dec. 19, 1978 [JP] Japan .................. 53-157180

[51] Int. Cl.³ ............... A01N 37/10; C07C 79/46
[52] U.S. Cl. .................... 71/108; 71/100;
260/455 R; 260/502.6; 560/21; 562/435
[58] Field of Search ............... 560/21; 71/108, 100;
260/455 R, 502.6; 562/435

[56] References Cited

U.S. PATENT DOCUMENTS

| 4,031,131 | 6/1977 | Johnson | 560/21 |
| 4,070,178 | 1/1978 | Johnson et al. | 560/21 |
| 4,088,474 | 5/1978 | Matterstock et al. | 560/21 |
| 4,093,446 | 6/1978 | Bayer et al. | 560/21 |
| 4,106,925 | 8/1978 | Rohr et al. | 560/21 |
| 4,134,753 | 1/1979 | Hörlein et al. | 560/21 |

Primary Examiner—Natalie Trousof
Assistant Examiner—G. T. Breitenstein
Attorney, Agent, or Firm—George B. Oujevolk

[57] ABSTRACT

Compounds of the general formula

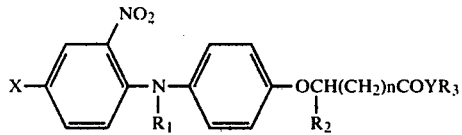

wherein
X is trifluoromethyl or halogen,
$R_1$ is hydrogen, lower alkyl, lower alkenyl or benzyl,
$R_2$ is lower alkyl,
$R_3$ is hydrogen, alkyl or alkali metal,
Y is oxygen or sulfur, and
n is 0, 1 or 2;

are useful as herbicides.

14 Claims, No Drawings

DIPHENYLAMINE DERIVATIVES

DETAILED DESCRIPTION OF THE INVENTION

The present invention relates to diphenylamine derivatives, to a process for the preparation thereof and their uses as selective herbicides.

In particular, this invention relates to herbicidally active compositions and to methods of killing undesired plants.

According to this invention, there is provided a compound of the formula [I]

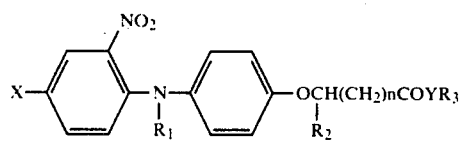

wherein
X is trifluoromethyl or halogen,
$R_1$ is hydrogen, lower alkyl such as those having 1 to 3 carbon atoms, lower alkenyl such as allyl, or benzyl,
$R_2$ is lower alkyl such as those having 1 to 3 carbon atoms,
$R_3$ is hydrogen, alkyl such as those having 1 to 12 carbon atoms, or alkali metal,
Y is oxygen or sulfur, and
n is 0, 1 or 2.

As an analogous compound which has herbicidal activity, 2,4-D(2,4-dichlorophenoxy acetic acid) is well-known, however it almost has not herbicidal activity to grass weeds. Further, it is disclosed in the Japanese Published Unexamined Patent Application No. 136138/1977 that m-anilino-phenoxypropionic acid derivatives are useful as medicines, and it is also suggested in the Patent Application that the m-anilino compounds have herbicidal activity to grass weeds.

The inventors have found that p-anilino compounds of this invention have outstanding herbicidal activity in the anilino-phenoxy carboxylic acid derivatives.

The compounds of this invention represented by the Formula [I] may be particularly effective for the control of grass weeds, such as barnyard grass (*Echinochloa crus-galli*), blackgrass (*Alopecurus myosuroides*), crabgrass (*Digitaria sanguinalis*), wild oat (*Avena fatua*) and Johnsongrass (*Sorghum halepense*), and they may hardly injure rice plants and broad leaf crops such as beans, peas, radish, beets and cucumber which easily suffer phyto-toxicity.

Adding to the herbicidal activity, the compounds of this invention have fungicidal activity. Furthermore, the compounds of this invention have analgesic, antihypertensive, antiinflammatory and antibiotic effect, and therefore, they are also useful for medicines.

Preferably in the formula [I], X is trifluoromethyl, chlorine, bromine or iodine, $R_1$ is hydrogen or lower alkyl of 1 to 3 carbon atoms, $R_2$ is lower alkyl of 1 to 3 carbon atoms, $R_3$ is lower alkyl of 1 to 3 carbon atoms, and n is zero. More preferably, X is trifluoromethyl, $R_1$ is hydrogen, $R_2$ is methyl, and Y is oxygen.

The compounds of this invention wherein $R_3$ is alkyl can be prepared in accordance with the following equations:

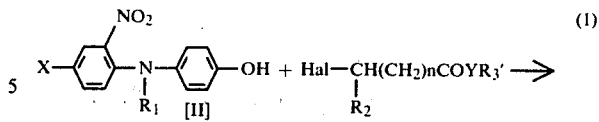

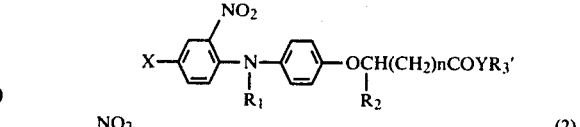

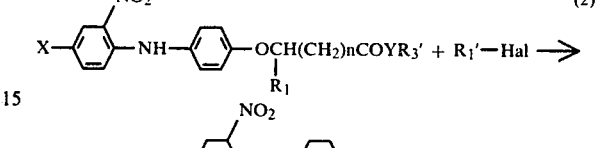

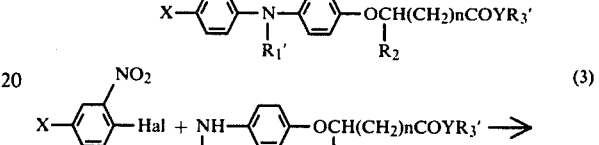

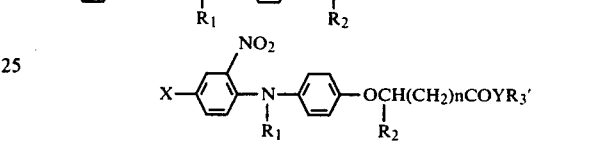

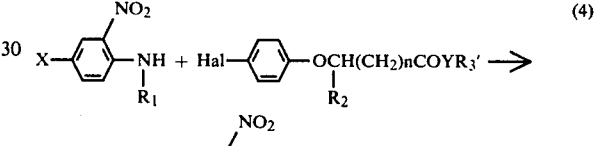

wherein X, $R_1$, $R_2$, Y and n are as defined previously, $R_1'$ is lower alkyl, lower alkenyl or benzyl, $R_3'$ is alkyl, and Hal is halogen such as chlorine or bromine.

The above reactions are carried out in an inert solvent in the presence of an alkaline condensing agent. The reactions may be performed by refluxing the reaction mixture for 3 to 6 hours. As an inert solvent, usual solvents such as acetone, methylethyl ketone, acetonitrile, dichloromethane, ethyl acetate isopropyl alcohol, ethylene glycol, dimethyl formamide, dimethyl sulfoxide, benzene, toluene, xylene, chlorobenzene and dichlorobenzene may be used.

As an alkaline condensing agent, potassium carbonate, sodium carbonate or sodium alcoholate such as methylate may be used.

After the reaction has been completed, the reaction solution is poured into chilled water, and the reaction product is extracted with an organic solvent. The organic solvent layer is washed with water and then dried. Removal of the solvent by distillation gives the ester compound of this invention. The carboxylic acid compound of this invention, namely the compound of the Formula [I] wherein $R_3$ is hydrogen, can be obtained by usual alkali hydrolysis of the ester compound. The altali metal salt of this invention can be obtained by the reaction of the carboxylic acid with alkali metal hydroxide such as sodium hydroxide or potassium hydroxide in an organic solvent.

The compound of this invention may be also produced according to the following equations:

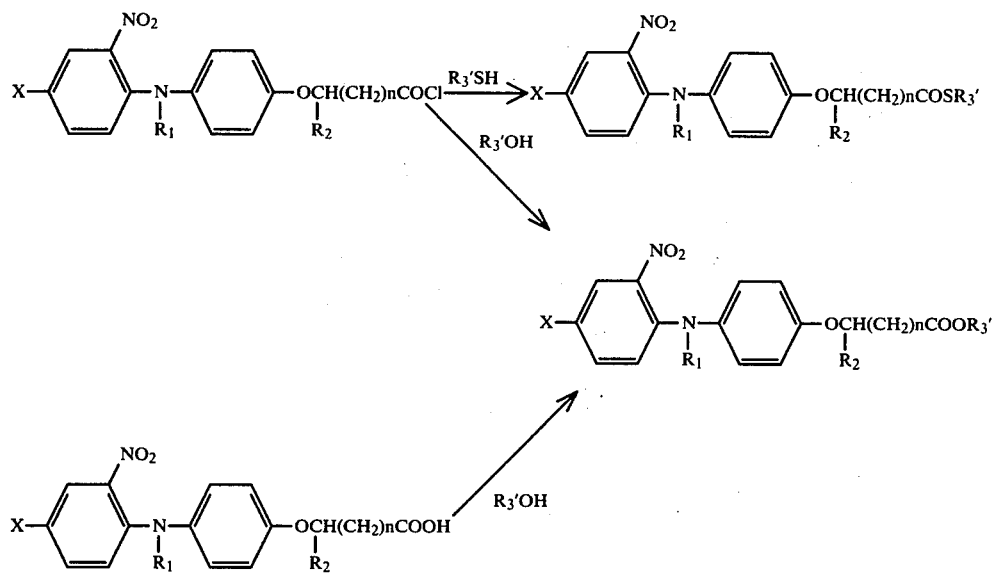

The starting material of the formula [II] may be prepared according to the following equation:

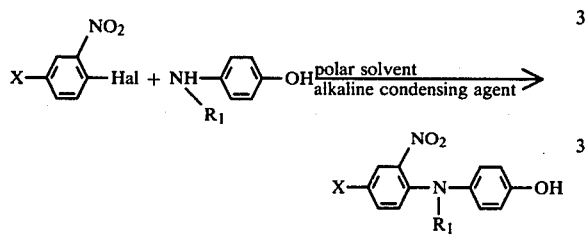

The following Examples illustrate production of compounds of this invention:

EXAMPLE 1

4-(2-nitro-4-trifluoromethylanilino) phenol 6.0 g of p-aminophenol was dissolved in 60 ml of isopropyl alcohol. To the solution was added 6.0 g of 4-chloro-3-nitro-benzotrifluoride and the resulting solution was heated under reflux for 12 hours. After the reaction, the solvent was removed by distillation and the residue was dissolved in benzene. The resulting solution was filtered and the solvent was removed from the filtrate by distillation. Thus, 7.5 g of the desired product was obtained.

m.p. 133°~134° C.

Ethyl 2-[4-(2-nitro-4-trifluoromethylanilino) phenoxy] propionate (Compound No. 1)

7.5 g of 4-(2-nitro-4-trifluoromethylanilino) phenol was dissolved in 80 ml of methylethyl ketone. To the solution were added 3.5 g of anhydrous potassium carbonate and then 4.6 g of ethyl 2-bromopropionate. The solution was heated under reflux for 5 hours. The resulting reaction solution was poured into water and extracted with ethyl acetate. The solution of ethyl acetate was washed with water and dried with anhydrous magnesium sulfate. 8.2 g of the desired compound was obtained by removing the solvent by distillation.

m.p. 61°~63° C.

EXAMPLE 2

2-[4-(2-nitro-4-trifluoromethylanilino) phenoxy] propionic acid (Compound No. 2)

A mixture of 2.0 g of ethyl 2-[4-(2-nitro-4-trifluoromethylanilino) phenoxy] propionate and 30 ml of 10% aqueous solution of sodium hydroxide was heated at 50° C. for one hour with stirring. After cooling, the reaction solution was acidified with concentrated hydrochloric acid. The precipitated crystals were filtered, washed with water and dried to obtain 1.7 g of the desired compound.

m.p. 158°~161° C.

EXAMPLE 3

Ethyl 2-[4-(4-chloro-2-nitroanilino) phenoxy] propionate (Compound No. 9)

11 g of 4-(4-chloro-2-nitroanilino) phenol was dissolved in 50 ml of methylethyl ketone. To the solution were added 5.8 g of anhydrous potassium carbonate and then 8.3 g of ethyl 2-bromopropionate. The solution was heated under reflux for 5 hours. The resulting reaction solution was treated as in Example 1 (Production of Compound No. 1) to obtain 13.5 g of the desired compound.

m.p. 46°~48° C.

EXAMPLE 4

Isopropyl 2-[4-(4-chloro-2-nitroanilino) phenoxy] propionate (Compound No. 11)

A mixture of 3 g of 2-[4-(4-chloro-2-nitroanilino) phenoxy] propionic acid, 1 g of isopropyl alcohol and one or two drops of concentrated sulfuric acid was heated under reflux for 4 hours, while issolating the produced water. After cooling, the reaction solution was washed with aqueous sodium carbonate and water, and then dried with anhydrous magnesium sulfate. Benzene was removed by distillation to obtain 3.1 g of the desired product.

m.p. 63°–65° C.

EXAMPLE 5

Ethyl 2-[4-(2-nitro-4-trifluoromethylanilino) phenoxy] thiolpropionate (Compound No. 15)

A solution of 3.7 g of 2-[4-(2-nitro-4-trifluoromethylanilino) phenoxy] propionic acid and 2.4 g of thionyl chloride in 40 ml of methylene chloride was heated under reflux for one hour. After the reaction, unreacted thionyl chloride was removed by distillation under reduced pressure together with the solvent. The residue was dissolved in methylene chloride. 0.7 g of ethylmercaptan and 1.2 g of triethylamine was added to the solution and the mixture was stirred for 12 hours at the room temperature. The resulting reaction solution was poured into water. The isolated methylene chloride layer was dried with magnesium sulfate and 3.2 g of the desired compound was obtained by removing the solvent by distillation under reduced pressure.

m.p. 55°–56° C.

EXAMPLE 6

Ethyl 2-[4-(2-nitro-4-trifluonomethylanilino) phenoxy] butyrate (Compound No. 18)

A mixture of 6 g of 4 -(2-nitro-4-trifluoromethylanilino) phenol, 60 ml of methylethyl ketone, 2.8 g of anhydrous potassium carbonate and 3.9 g of ethyl 2-bromobutyrate was heated under reflux for 5 hours. The resulting reaction mixture was treated as in Example 1 to obtain 7.8 g of the desired compound.

m.p. 60°–62° C.

EXAMPLE 7

Ethyl 4-[4-(2-nitro-4-trifluoromethylanilino) phenoxy] valerate (Compound No. 19)

A mixture of 6 g of 4-(2-nitro-4-trifluoromethylanilino) phenol, 60 ml of dimethylformamide, 2.8 g of anhydrous potassium carbonate and 3.3 g of 4-chlorovaleric acid was heated at 120° to 130° C. for 5 hours with stirring. The resuting reaction mixture was treated as in Example 1 to obtain 7.7 g of the desired compound.

m.p. 60°–62° C.

EXAMPLE 8

Ethyl 2-[4-(N-methyl-2-nitro-4-trifluoromethylanilino) phenoxy] propionate (Compound No. 21)

A mixture of 3.1 g of 4-(N-methyl-2-nitro-4-trifluoromethylamilino) phenol, 30 ml of methylethyl ketone, 1.4 g anhydrous potassium carbonate and 1.8 g of ethyl 2-bromopropionate was heated under reflux for 5 hours. The resulting reaction mixture was treated as in Example 1 to obtain 3.8 g of the desired compound.

m.p. 88°–89° C.

EXAMPLE 9

Ethyl 2-[4-(N-allyl-2-nitro-4-trifluoromethylanilino) phenoxy] propionate (Compound No. 23)

0.26 g of sodium hydride (50% oil suspension) was gradually added to a solution of 2 g of ethyl 2-[4-(2-nitro-4-trifluoromethylanilino) phenoxy] propionate in 50 ml of dimethylformamide at 0° C. or below with stirring. After the generation of hydrogen gas had stopped, the mixture was kept at 0° C. or below for one hour, and then left overnight at room temperature. The reaction mixture was poured into water and extracted with ethylacetate to obtain a crude product. The crude product was purified by silica gel chromatography to obtain 1.2 g of the desired compound as oily red substance.

$n_D^{31.5}$ 1.5550

Examples of compounds of this invention are listed in Table 1.

TABLE 1

$$X-\underset{}{\underset{NO_2}{\bigcirc}}-N(R_1)-\bigcirc-OCH(R_2)(CH_2)_nCOYR_3$$

| Compound No. | X | $R_1$ | $R_2$ | $R_3$ | Y | n | Physical Constant [m.p.]°C. |
|---|---|---|---|---|---|---|---|
| 1 | $CF_3$ | H | $CH_3$ | $C_2H_5$ | 0 | 0 | [61–63] |
| 2 | " | " | " | H | " | " | [158–161] |
| 3 | " | " | " | $CH_3$ | " | " | [111–113] |
| 4 | " | " | " | Na | " | " | [215–219] |
| 5 | " | " | " | $C_3H_7^i$ | " | " | [72–74] |
| 6. | " | " | " | $C_3H_7^n$ | " | " | [57–60] |
| 7 | Cl | " | " | H | " | " | [175–177] |
| 8 | " | " | " | $CH_3$ | " | " | [59–61] |
| 9 | " | " | " | $C_2H_5$ | " | " | [46–48] |
| 10 | " | " | " | $C_3H_7^n$ | " | " | [60–63] |
| 11 | " | " | " | $C_3H_7^i$ | " | " | [63–65] |
| 12 | " | " | " | $C_2H_5$ | S | " | $n_D^{32.5}$ 1.6585 |
| 13 | " | " | " | Na | O | " | [180–190] |
| 14 | Br | " | " | $C_2H_5$ | " | " | [68–70] |
| 15 | $CF_3$ | " | " | " | S | " | [55–56] |
| 16 | Br | " | " | $C_3H_7^i$ | O | " | [59–61] |

TABLE 1-continued $$X-\underset{\underset{R_1}{|}}{C_6H_3(NO_2)}-N-C_6H_4-OCH(CH_2)_nCOYR_3$$
with $R_2$ on the OCH group

| Compound No. | X | $R_1$ | $R_2$ | $R_3$ | Y | n | Physical Constant [m.p.]°C |
|---|---|---|---|---|---|---|---|
| 17 | " | " | " | $CH(C_2H_5)(CH_3)$ (CH-CH3 with C2H5) | " | " | $n_D^{27}$ 1.6252 |
| 18 | $CF_3$ | " | $C_2H_5$ | $C_2H_5$ | " | " | [60–62] |
| 19 | " | " | $CH_3$ | " | " | 2 | [60–62] |
| 20 | " | " | $C_3H_7{}^i$ | " | " | 0 | $n_D^{30}$ 1.5725 |
| 21 | " | $CH_3$ | $CH_3$ | " | " | " | [88–89] |
| 22 | " | $C_2H_5$ | " | " | " | " | [81–85] |
| 23 | " | $CH_2CH=CH_2$ | " | " | " | " | $n_D^{31.5}$ 1.5550 |
| 24 | " | $CH_2$–$C_6H_5$ | " | " | " | " | $n_D^{23}$ 1.5770 |
| 25 | " | $C_3H_7{}^n$ | " | " | " | " | [69–71] |
| 26 | " | $C_2H_5$ | " | $CH_3$ | " | " | [62–64] |
| 27 | " | " | " | $C_3H_7{}^i$ | " | " | [88–89] |
| 28 | " | " | " | $CH_2CH(CH_3)_2$ | " | " | $n_D^{24}$ 1.5481 |
| 29 | I | H | " | $C_2H_5$ | " | " | [70–71] |
| 30 | " | " | " | $C_3H_7{}^i$ | " | " | [56–58] |
| 31 | Cl | $C_2H_5$ | " | $C_2H_5$ | " | " | [62–65] |
| 32 | Cl | $CH_2CH=CH_2$ | $CH_3$ | $C_2H_5$ | O | 0 | [44–46] |
| 33 | $CF_3$ | $C_2H_5$ | " | H | " | " | [126–128] |
| 34 | " | H | " | $C_{12}H_{25}$ | " | " | $n_D^{24.5}$ 1.5440 |
| 35 | " | " | " | $C_4H_9{}^n$ | " | " | [75–76] |
| 36 | " | " | " | $C_6H_{13}{}^n$ | " | " | $n_D^{25}$ 1.5640 |
| 37 | " | " | " | $C_8H_{17}{}^n$ | " | " | $n_D^{25}$ 1.5562 |
| 38 | " | " | " | $C_5H_{11}{}^n$ | " | " | [47–48] |
| 39 | " | " | " | $C_4H_9{}^i$ | " | " | [83–85] |
| 40 | Cl | " | " | " | " | " | [30–31] |
| 41 | $CF_3$ | $CH_2CH=CH_2$ | " | " | " | " | $n_D^{21}$ 1.5457 |
| 42 | I | H | " | H | " | " | [159–160] |
| 43 | $CF_3$ | $CH_2CH=CH_2$ | " | " | " | " | $n_D^{20}$ 1.5515 |
| 44 | Cl | $CH_2$–$C_6H_5$ | " | $C_2H_5$ | " | " | |

As mentioned previously, the compounds of this invention possess superior herbicidal activity. The compounds may be applied directly to the soil as pre-emergence treatment or as post-emergence treatment to plant foliage. The preferred treatment is after emergence of the plant foliage and the compounds may be applied to soil or to plant foliage in amounts of 10 g or more per 10 are.

A herbicidal composition having a compound of this invention as its active ingredient may be formulated by mixing suitable carriers in a form generally used in agricultural chemicals, such as wettable powder, emulsifiable concentrate, granular formulation, water soluble powder and aerosol. As solid carriers, bentonite, diatomaceous earth, apatite, gypsum, talc, pyrophllite, vermiculite and clay may be used. As liquid carriers, water, kerosine, mineral oil, petrolium, solvent naphtha, benzene, xylene, cyclohexane, cyclohexanone, dimethylformamide, alcohol and acetone may be used. A surface active agent may also be added, in order to give a homogeneous and stable formulation.

Compounds of this invention can also be applied admixed with other chemicals, which are used in agronomic and horticultural management and which are compatible with such compounds. Such chemicals can be, but are not restricted to, the classes of chemical commonly known as plant nutrients, fertilizers, insecticides, acaridides, fungicides, herbicides and nematocides.

For admixture of the compound with known herbicides, the use is recommended of triazine derivatives such as simazine, propazine and prometryn, carbamate derivatives such as phenmedipham, urea derivatives such as metabenzthiazuron and linuron, heterocyclic compounds such as pyrazon and lenacil, and phenoxy alkane carboxylic acid derivatives such as 2,4-D.

The concentration of the active ingredient in a herbicidal composition of this invention may vary according to type of formulation, and the concentration is, for example, in the range of 5–80 weight percent, preferably 10–60 weight percent, in wettable powder; 5–70 weight percent, preferably 20–60 weight percent, in emulsifiable concentrates; and 0.5–30 weight percent, preferably 1–10 weight percent, in granular formulation.

A wettable powder or an emulsifiable concentrate thus produced may be diluted with water to a specified concentration and used as a liquid suspension or a liquid emulsion for treating soils or plant foliage. Further, a granular formulation may be directly used for soil treatment.

Non-limiting examples of herbicidal compositions according to the invention are as follows:

EXAMPLE 10

Wettable Powder

| | Parts by weight |
|---|---|
| Compound No. 1 | 30 |
| White carbon | 6 |
| Diatomaceous earth | 56 |
| Sodium alkylsulfate | 8 |

These are mixed homogeneously and reduced to fine particles to provide a wettable powder containing 30% of active ingredient. In use, it is diluted to a desired concentration with water, and is sprayed as a suspension.

EXAMPLE 11

Emulsifiable Concentrate

| | Parts by weight |
|---|---|
| Compound No. 8 | 25 |
| Xylene | 20 |
| Dimethylformamide | 47 |
| Polyoxyethylene phenylether | 8 |

These are mixed together to provide an emulsifiable concentrate containing 25% of the active ingredient. In use, it is diluted to a desired concentration with water, and is sprayed as an emulsion.

EXAMPLE 12

Granular Formulation

| | Parts by weight |
|---|---|
| Compound No. 15 | 3 |
| Talc | 85 |
| Bentonite | 8 |
| Polyoxyethylene alkylarylsulfate | 4 |

These are mixed homogeneously and reduced to fine particles. The fine particles are made into granules, each having a diameter in the range of 0.5-1.0 mm, to provide a granular formulation containing 3% of the active ingredient. In use it is directly applied.

The herbicidal effects of compounds of this invention are illustrated by the following tests:

TEST 1

Pre-Emergence

Seeds of crabgrass, wild oat, lamb's-quarters, pig weed, chrysanthemum coronarium and soybean were planted in each pot having a surface area of 250 cm2, and instantly, an aqueous suspension prepared by diluting an emulsifiable concentrate with water to a specified concentration was sprayed on the soil surface at a rate of 200 g of active ingredient per 10 are. The pots were kept in a green house. Three weeks after spraying, the degree of damage to the each plant was observed and evaluated on the scale of values of 0~10 which has the following meanings:

0: no effect
10: plant completely killed or no germination

The results are shown in Table 2.

TABLE 2

| Compound No. | crab-grass | wild-oat | lamb's-quarters | pig weed | chrysanthemum coronarium | soy-bean |
|---|---|---|---|---|---|---|
| 1 | 10 | 9 | 0 | 0 | 0 | 0 |
| 2 | 10 | 10 | 0 | 0 | 0 | 0 |
| 3 | 10 | 10 | 0 | 0 | 0 | 0 |
| 4 | 10 | 9 | 0 | 0 | 0 | 0 |
| 5 | 10 | 10 | 0 | 0 | 0 | 0 |
| 6 | 10 | 3 | 0 | 0 | 0 | 0 |
| 7 | 9 | 4 | 0 | 0 | 0 | 0 |
| 8 | 9 | 7 | 0 | 0 | 0 | 0 |
| 9 | 10 | 10 | 0 | 0 | 0 | 0 |
| 10 | 9 | 5 | 0 | 0 | 0 | 0 |
| 11 | 10 | 6 | 0 | 0 | 0 | 0 |
| 12 | 8 | 6 | 0 | 0 | 0 | 0 |
| 13 | 8 | 2 | 0 | 0 | 0 | 0 |
| 14 | 9 | 7 | 0 | 0 | 0 | 0 |
| 15 | 10 | 10 | 0 | 0 | 0 | 0 |
| 16 | 10 | 8 | 0 | 0 | 0 | 0 |
| 17 | 10 | 7 | 0 | 0 | 0 | 0 |
| 18 | 10 | 8 | 0 | 0 | 0 | 0 |
| 19 | 10 | 3 | 0 | 0 | 0 | 0 |
| 21 | 10 | 10 | 0 | 0 | 0 | 0 |
| 22 | 10 | 9 | 0 | 0 | 0 | 0 |
| 23 | 10 | 10 | 0 | 0 | 0 | 0 |
| 24 | 6 | 3 | 0 | 0 | 0 | 0 |
| 25 | 10 | 8 | 0 | 0 | 0 | 0 |
| 26 | 10 | 5 | 0 | 0 | 0 | 0 |
| 27 | 10 | 7 | 0 | 0 | 0 | 0 |
| 28 | 10 | 7 | 0 | 0 | 0 | 0 |
| 29 | 8 | 0 | 0 | 0 | 0 | 0 |
| 30 | 6 | 0 | 0 | 0 | 0 | 0 |
| 31 | 8 | 1 | 0 | 0 | 0 | 0 |
| 32 | 9 | 2 | 0 | 0 | 0 | 0 |
| 33 | 10 | 9 | 0 | 0 | 0 | 0 |
| 34 | 10 | 1 | 0 | 0 | 0 | 0 |
| 35 | 10 | 5 | 0 | 0 | 0 | 0 |
| 36 | 10 | 6 | 0 | 0 | 0 | 0 |
| 37 | 10 | 4 | 0 | 0 | 0 | 0 |
| 38 | 10 | 3 | 0 | 0 | 0 | 0 |
| 39 | 10 | 3 | 0 | 0 | 0 | 0 |
| 40 | 10 | 2 | 0 | 0 | 0 | 0 |
| 42 | 9 | 1 | 0 | 0 | 0 | 0 |
| 43 | 10 | 7 | 0 | 0 | 0 | 0 |
| 44 | 8 | 1 | 0 | 0 | 0 | 0 |
| *Comparative compound 1. | 2 | 1 | 10 | 10 | 10 | 10 |
| 2. | 0 | 0 | 1 | 0 | 1 | 1 |

* *Comparative compound
1. 2,4-D : 2,4-dichlorophenoxy acetic acid

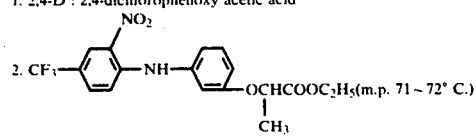

2. $CF_3$—⟨NO_2⟩—NH—⟨⟩—OCHCOOC$_2$H$_5$(m.p. 71~72° C.)
           |
           CH$_3$

TEST 2

Post-Emergence

Seeds of crabgrass, wild oat, lamb's-quarters and pig weed were planted in each pot having a surface area of 200 cm2. When the plants were grown to 2-4 leaves stage, an aqueous suspension, prepared by diluting an emulsifiable concentrate with water to a specified concentration was sprayed on the foliage of the test plants at a rate of 200 g of active ingredient per 10 are, and the pots were kept in a green-house. Three weeks after spraying, the degree of damage to the each plant was observed and evaluated on the same scale as in test 1.

The results are shown in Table 3.

TABLE 3

| Compound No. | crabgrass | wild oat | lamb's-quarters | pig weed |
| --- | --- | --- | --- | --- |
| 1 | 10 | 10 | 0 | 0 |
| 2 | 10 | 10 | 0 | 0 |
| 3 | 10 | 10 | 0 | 0 |
| 4 | 10 | 10 | 0 | 0 |
| 5 | 10 | 10 | 0 | 0 |
| 6 | 10 | 10 | 0 | 0 |
| 7 | 10 | 10 | 0 | 0 |
| 8 | 10 | 10 | 0 | 0 |
| 9 | 10 | 10 | 0 | 0 |
| 10 | 10 | 10 | 0 | 0 |
| 11 | 10 | 10 | 0 | 0 |
| 12 | 10 | 10 | 0 | 0 |
| 13 | 10 | 10 | 0 | 0 |
| 14 | 10 | 10 | 0 | 0 |
| 15 | 10 | 10 | 0 | 0 |
| 16 | 10 | 10 | 0 | 0 |
| 17 | 10 | 10 | 0 | 0 |
| 18 | 10 | 10 | 0 | 0 |
| 19 | 10 | 7 | 0 | 0 |
| 21 | 6 | 8 | 0 | 0 |
| 22 | 10 | 10 | 0 | 0 |
| 23 | 10 | 10 | 0 | 0 |
| 24 | 6 | 7 | 0 | 0 |
| 25 | 10 | 10 | 0 | 0 |
| 26 | 9 | 10 | 1 | 0 |
| 27 | 3 | 10 | 0 | 0 |
| 28 | 9 | 10 | 0 | 0 |
| 29 | 10 | 10 | 2 | 1 |
| 30 | 10 | 10 | 0 | 0 |
| 31 | 4 | 10 | 0 | 0 |
| 32 | 1 | 7 | 0 | 0 |
| 33 | 5 | 10 | 0 | 0 |
| 34 | 7 | 3 | 0 | 0 |
| 35 | 10 | 10 | 0 | 0 |
| 36 | 10 | 10 | 0 | 0 |
| 37 | 10 | 10 | 0 | 0 |
| 38 | 10 | 10 | 0 | 0 |
| 39 | 10 | 10 | 0 | 0 |
| 40 | 10 | 10 | 0 | 0 |
| 42 | 10 | 10 | 0 | 0 |
| 43 | 10 | 10 | 0 | 0 |
| 44 | 10 | 10 | 5 | 5 |
| *Comparative Compound | | | | |
| 1 | 3 | 1 | 10 | 10 |
| 2 | 1 | 0 | 1 | 1 |

*Comparative compound 1 and 2 : the same as in Test 1

We claim:

1. A compound of the general formula

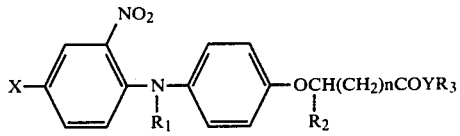

wherein
X is trifluoromethyl or halogen,
$R_1$ is hydrogen, lower alkyl, lower alkenyl or benzyl
$R_2$ is lower alkyl
$R_3$ is hydrogen, alkyl or alkali metal
Y is oxygen or sulfur
n is 0, 1 or 2.

2. A compound according to claim 1, wherein
$R_1$ is hydrogen, lower alkyl of 1 to 3 carbon atoms, allyl or benzyl,
$R_2$ is lower alkyl of 1 to 3 carbon atoms, and $R_3$ is hydrogen, alkyl of 1 to 12 carbon atoms or alkali metal.

3. A compound according to claim 2, wherein $R_1$ is hydrogen, $R_2$ is methyl, $R_3$ is lower alkyl of 1 to 3 carbon atoms and n is zero.

4. A compound according to claim 3, wherein X is trifluoromethyl and Y is oxygen.

5. A compound according to claim 3, wherein X is halogen.

6. A compound according to claim 2, wherein X is trifluoromethyl, $R_1$ and $R_3$ are lower alkyl of 1 to 3 carbon atoms, and Y is oxygen.

7. A herbicidal composition, comprising an inert carrier and an effective amount of a compound of claim 1.

8. A herbicidal composition, comprising an inert carrier and an effective amount of a compound of claim 2.

9. A herbicidal composition, comprising an inert carrier and an effective amount of a compound of claim 3.

10. A herbicidal composition, comprising an inert carrier and an effective amount of a compound of claim 4.

11. A herbicidal composition, comprising an inert carrier and an effective amount of a compound of claim 5.

12. A herbicidal composition, comprising an inert carrier and an effective amount of a compound of claim 6.

13. A method for the control of weeds, comprising applying to the locus to be protected an effective amount of a compound of claim 1.

14. A compound according to claim 1, wherein X is $CF_3$, $R_1$ is H, $R_2$ is methyl, n is zero, Y is oxygen and $R_3$ is ethyl.

* * * * *